US012760452B2

(12) United States Patent
Russo et al.

(10) Patent No.: US 12,760,452 B2
(45) Date of Patent: Oct. 13, 2026

(54) METHOD FOR MAKING BRAIDED MEDICAL DEVICES

(71) Applicant: KA Medical, LLC, Roseville, MN (US)

(72) Inventors: Pat Russo, Vadnais Heights, MN (US); Bill Riewer, Elk River, MN (US); John Oslund, Blaine, MN (US)

(73) Assignee: KA Medical, LLC, Roseville, MN (US)

( * ) Notice: Subject to any disclaimer, the term of this patent is extended or adjusted under 35 U.S.C. 154(b) by 0 days.

(21) Appl. No.: 18/540,646

(22) Filed: Dec. 14, 2023

(65) Prior Publication Data

US 2024/0188947 A1 Jun. 13, 2024

Related U.S. Application Data

(63) Continuation of application No. 17/217,779, filed on Mar. 30, 2021, now Pat. No. 11,896,207.

(Continued)

(51) Int. Cl.

*D04C 3/48* (2006.01)
*A61B 17/00* (2006.01)
*D04C 1/06* (2006.01)

(52) U.S. Cl.

CPC ............ *D04C 3/48* (2013.01); *A61B 17/0057* (2013.01); *D04C 1/06* (2013.01);

(Continued)

(58) Field of Classification Search

CPC ........ D04C 3/48; D04C 1/06; A61B 17/0057; A61B 2017/00526; A61B 2017/00606; A61B 2017/00867

See application file for complete search history.

(56) References Cited

U.S. PATENT DOCUMENTS 2,978,023 A * 4/1961 Helland .................... D21F 1/10 28/142
6,123,715 A 9/2000 Amplatz (Continued)

FOREIGN PATENT DOCUMENTS

FR 361387 * 6/1906
WO WO-2017205617 A1 * 11/2017 ....... A61B 17/12113
WO WO-2020060587 A1 * 3/2020 ....... A61B 17/12122

OTHER PUBLICATIONS

Partial European Search Report dated Feb. 22, 2024 for EP21779569.9.

(Continued)

*Primary Examiner* — Shaun R Hurley

(74) *Attorney, Agent, or Firm* — Dorsey & Whitney LLP

(57) ABSTRACT

A method for making a braided medical device may involve positioning an insert inside a braided material, processing the braided material to form the braided medical device, dissolving and/or crushing the insert into multiple pieces, and removing the multiple pieces from the braided medical device. In some embodiments, the insert is made of gypsum. A braided medical device for occluding a defect in a heart may include a right disc for residing in a right side of the heart, a left disc having a partially circular shape for residing in a left side of the heart, and a waist extending between the right disc and the left disc and having a smaller diameter than that of either the right disc or the left disc.

12 Claims, 6 Drawing Sheets

Related U.S. Application Data

(60) Provisional application No. 63/004,252, filed on Apr. 2, 2020.

(52) U.S. Cl.
CPC ............... *A61B 2017/00526* (2013.01); *A61B 2017/00606* (2013.01); *A61B 2017/00867* (2013.01)

(56) References Cited

U.S. PATENT DOCUMENTS

| | | | | |
|---|---|---|---|---|
| 10,327,781 | B2 * | 6/2019 | Divino | A61B 17/12022 |
| 11,896,207 | B2 * | 2/2024 | Russo | A61B 17/0057 |
| 2002/0123759 | A1 | 9/2002 | Amplatz | |
| 2005/0228434 | A1 | 10/2005 | Amplatz et al. | |
| 2006/0241690 | A1 | 10/2006 | Amplatz et al. | |
| 2007/0265656 | A1 | 11/2007 | Amplatz et al. | |
| 2007/0270943 | A1 | 11/2007 | Solem et al. | |
| 2012/0301654 | A1 * | 11/2012 | Wetzels | B29C 70/865 242/434.6 |
| 2013/0041404 | A1 | 2/2013 | Amin et al. | |
| 2014/0296909 | A1 | 10/2014 | Heipl et al. | |
| 2017/0056065 | A1 | 3/2017 | Do et al. | |
| 2017/0273790 | A1 | 9/2017 | Vettukattil et al. | |
| 2018/0070955 | A1 * | 3/2018 | Greene, Jr. | A61B 17/1204 |
| 2019/0000608 | A1 | 1/2019 | Renke | |
| 2019/0046684 | A1 | 2/2019 | Roth | |
| 2019/0076136 | A1 | 3/2019 | Zhang et al. | |
| 2019/0358063 | A1 | 11/2019 | Walsh et al. | |
| 2021/0307735 | A1 | 10/2021 | Russo et al. | |

OTHER PUBLICATIONS

International Search Report and Written Opinion dated Jul. 21, 2021 for PCT/US2021/024981.
Notice of Allowance dated Oct. 17, 2023 for U.S. Appl. No. 17/217,779.
Office Action dated Mar. 15, 2023 for U.S. Appl. No. 17/217,779.
Office Action dated Jun. 30, 2023 for U.S. Appl. No. 17/217,779.

* cited by examiner

METHOD FOR MAKING BRAIDED MEDICAL DEVICES

RELATED APPLICATIONS

This application is a Continuation of U.S. patent application Ser. No. 17/217,779, filed Mar. 30, 2021, titled "Method for Making Braided Medical Devices," which claims priority to U.S. Provisional Application No. 63/004,252, filed on Apr. 2, 2020 and titled, "Method for Making Braided Medical Devices," which are both hereby incorporated by reference in their entireties.

TECHNICAL FIELD

The present application is related to medical devices and methods. More specifically, the application is related to braided medical devices and methods for manufacturing them. In some embodiments, the application is related to braided medical devices for treating a heart defect and methods of manufacturing them.

DETAILED DESCRIPTION

Figure 1A:
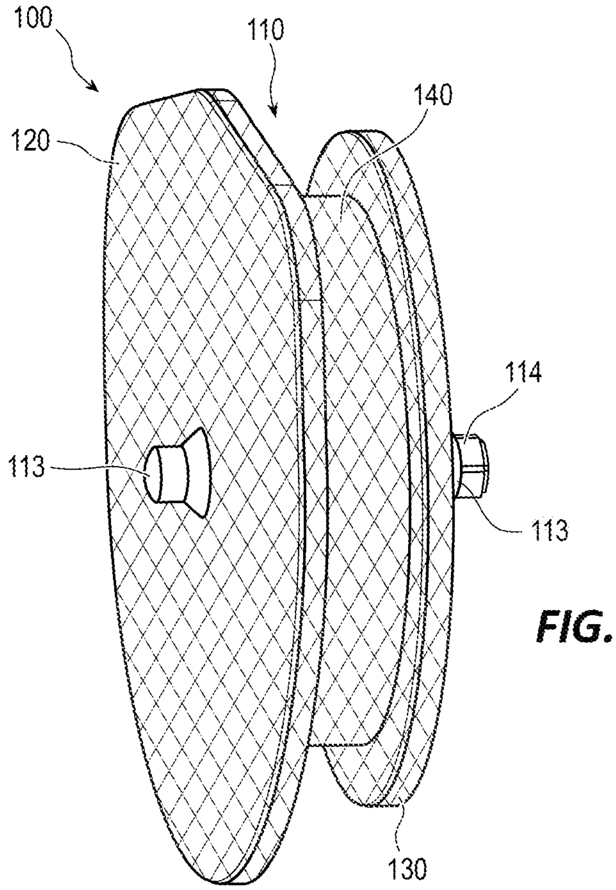
FIG. 1A is a perspective diagrammatic view of an embodiment of a braided medical device configured for treating a ventricular septal defect (VSD).

Braided medical devices are used for many different applications in the body. In some instances, implantable braided devices may be used in vascular and cardiovascular procedures to prop open a blood vessel, act as a filter for capturing blood clots, occlude a blood vessel, occlude a congenital or structural cardiac defect, act as a support structure for an artificial valve, and the like.

Braided devices may be made of multiple wires, including, in some embodiments, one or more wires made of a shape memory material, such as Nitinol. Braiding may be a subassembly process, rather than a single finished device manufacturing process. For example, in some instances, to manufacture a braided medical device, the braid is produced in bulk over long (relative to the device length), typically cylindrical mandrels and then later cut to discrete lengths for further processing. These discrete lengths of braid may be combined with other components, such as radiopaque marker bands, and shape set ("formed") into finished devices. The forming process involves transforming the braid into different shapes through the use of molds to define the outer profile and inserts placed inside the braid to support and define the inner profile, and then using heating and quenching to affect a phase transformation in the braid material and thus set the final shape of the device. The device is then removed from the mold and the inserts inside the device are removed.

Braided devices can have varying degrees of complexity. A simple braided device, such as a stent or graft, could be a basic cylinder and may utilize a very basic mold and insert to form. A more complex device, such as a vascular occluder or cardiac defect occluder, might have multiple "lobes" of differing diameters, widths, and shapes. The mold used to define the outer profile of a more complex device may comprise an assembly of multiple parts, and the inserts used to support and define the inner profile of the device may also comprise multiple parts. Some braided devices are also constructed from multiple layers of braid, where there may be intentional separation or offset between layers, thus creating another level of manufacturing complexity.

As the complexity of braided device geometry increases, so do the manufacturing challenges. In some processes, it may be particularly challenging to place inserts inside the braid prior to forming the device and then removing the inserts after forming. Traditional forming of devices that require the use of internal support may necessitate forcing openings in the braid to manually insert coils, rings, discs, slugs, barrels, plates, or the like inside the braid and/or between one or more layers of braid in the same device. However, such processes and components can result in increased scrap, increased cost, higher level of required operator skill, distortion and deformation of the braided structure, breaking of one or more individual wires, compromising the integrity of attached components such as marker bands, compromising performance and effectiveness of the overall device if implanted, and other challenges and issues.

An embodiment of a braided medical device within the scope of this disclosure can be used to occlude a heart defect, such as a ventricular septal defect (VSD). The device includes a right disc for residing in a right side of the heart; a left disc for residing in a left side of the heart; and a waist extending between the right disc and the left disc. An upper portion of the left disc may be non-circular and configured to be positioned on a subaortic rim of an aortic valve of the heart. A diameter of the waist may be less than a diameter of the left disc and a diameter of the right disc. The device can include a shape memory material, such as Nitinol. The device can include an outer braided layer and an inner braided layer. In some embodiments, the inner braided layer can be stiffer than the outer braided layer. The waist can include a space or gap disposed between the outer braided layer and the inner braided member. Radiopaque markers may be coupled to the ends of the device. A threaded connector may also be coupled to one of the radiopaque markers to facilitate coupling of the device to a delivery wire. Additionally, in some embodiments, a fabric, such as polyester, can be coupled to the device to facilitate occlusion of the heart defect.

A method for making braided medical devices, such as the device described herein, involves using a frangible (such as dissolvable and/or crushable) material for one or more inserts disposed within the device during a device forming process. The insert(s) may then be removed from the device by dissolving, crushing, or otherwise breaking down the insert(s). In one embodiment, the material used for the insert(s) is gypsum (calcium sulfate dihydrate), although alternative embodiments may use other frangible materials, including dissolvable and/or crushable materials.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Figure 1B:
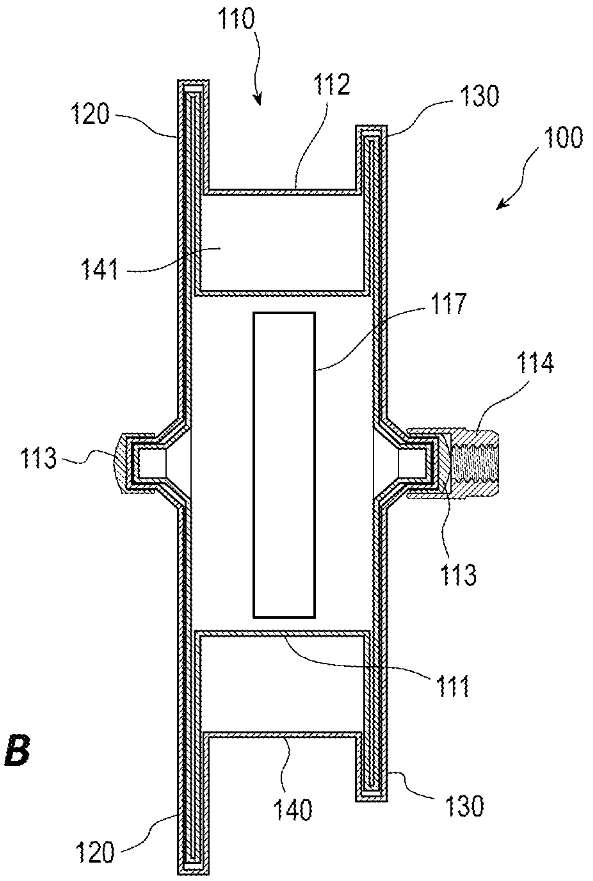
FIG. 1B is a side cross-sectional diagrammatic view of the braided medical device of FIG. 1A.
Figure 2:
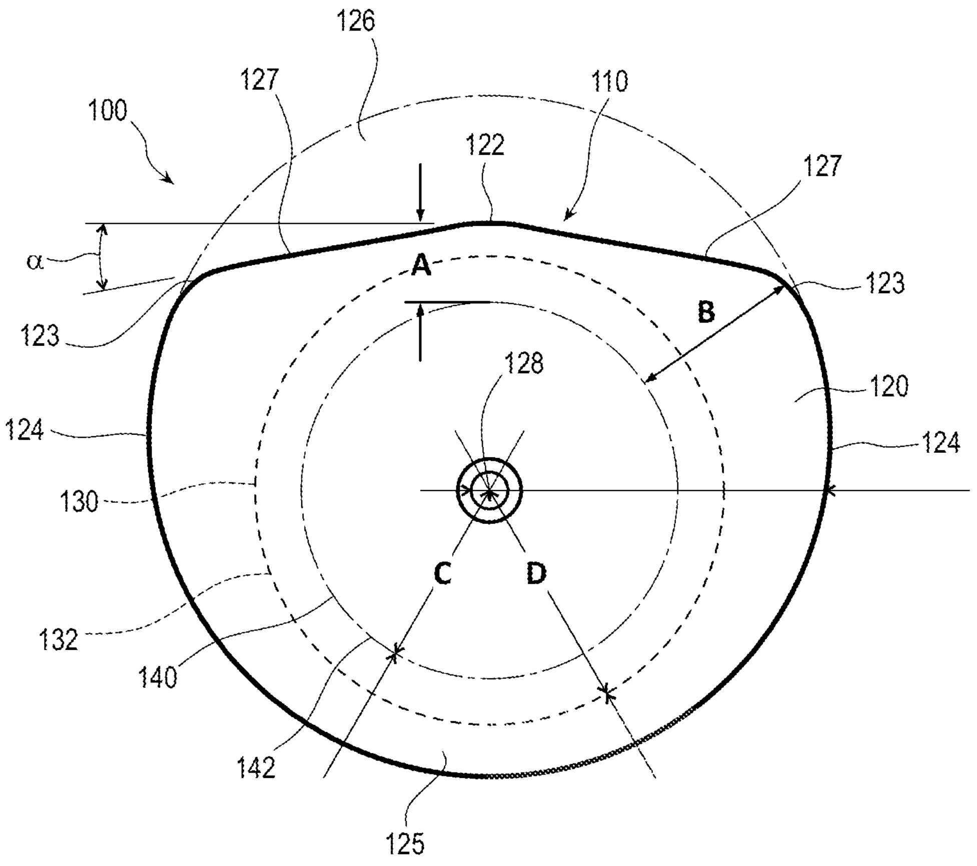
FIG. 2 is a left-sided diagrammatic view of the braided medical device of FIG. 1A.
Figure 3:
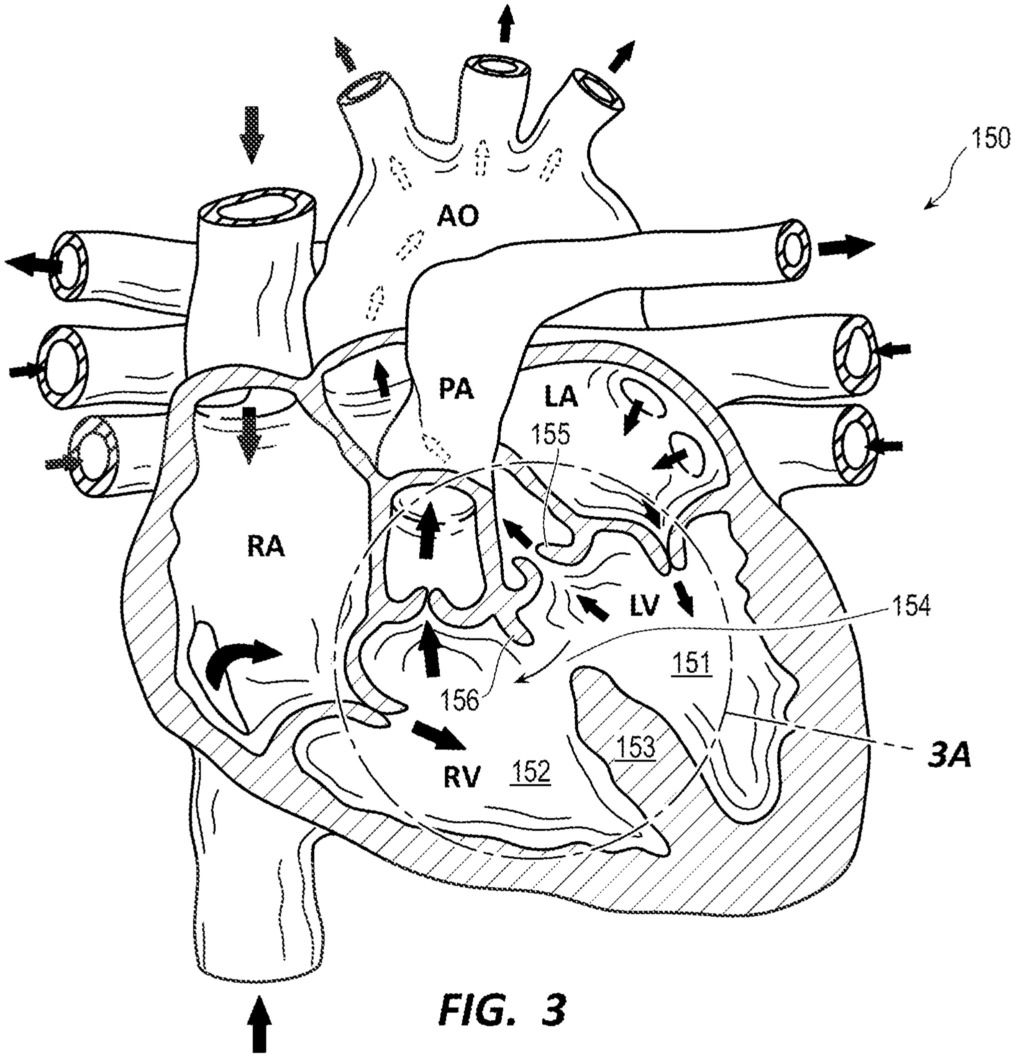
FIG. 3 is a diagrammatic cross-sectional view of a human heart with a VSD.
Figure 3A:
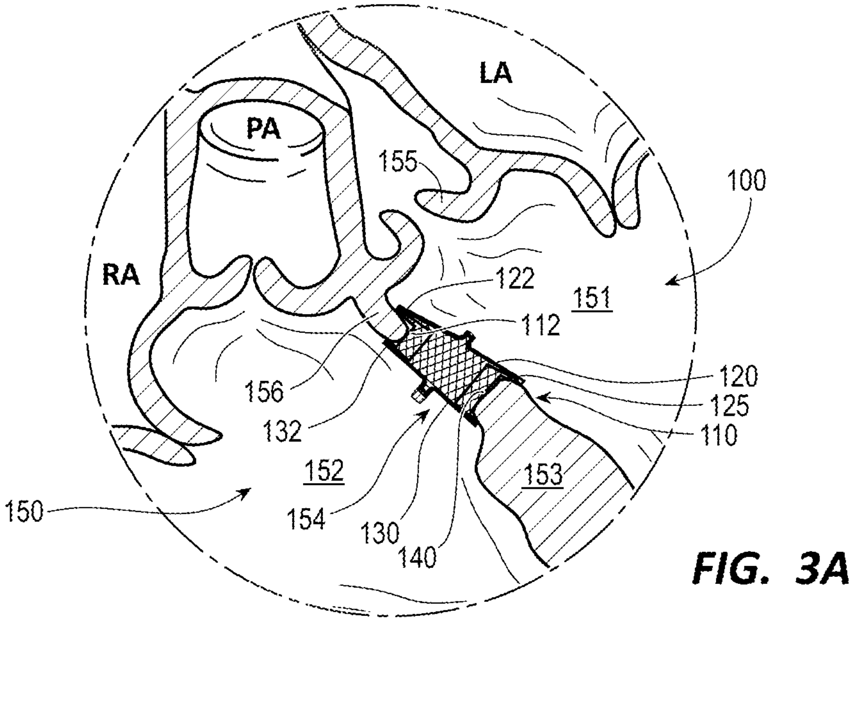
FIG. 3A is a close-up view of the VSD of FIG. 3, with the braided medical device of FIG. 1A disposed within the VSD.
Figure 4:
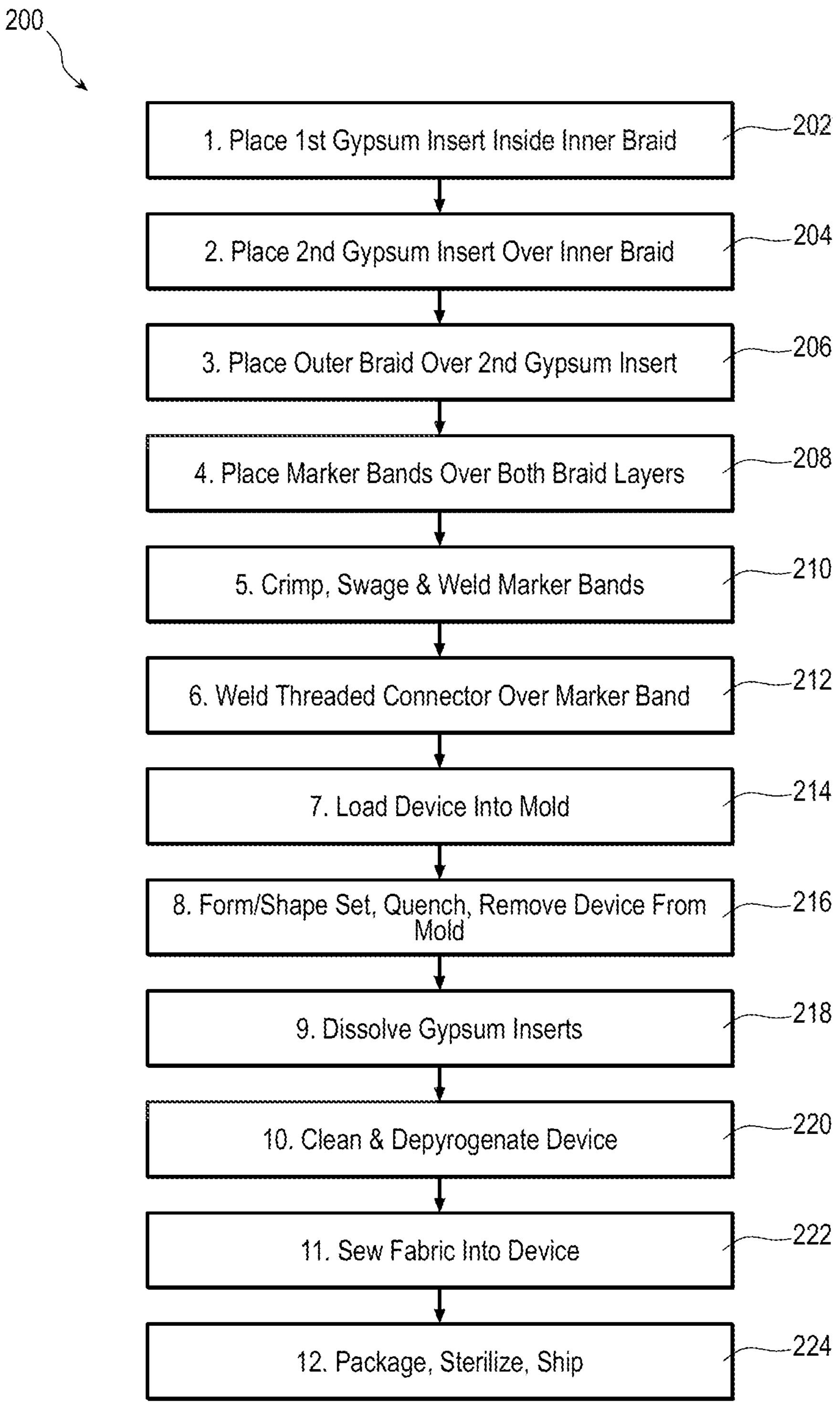
FIG. 4 is a flow chart illustrating an embodiment of a manufacturing process for making the braided medical device of FIG. 1A.
Figure 5:
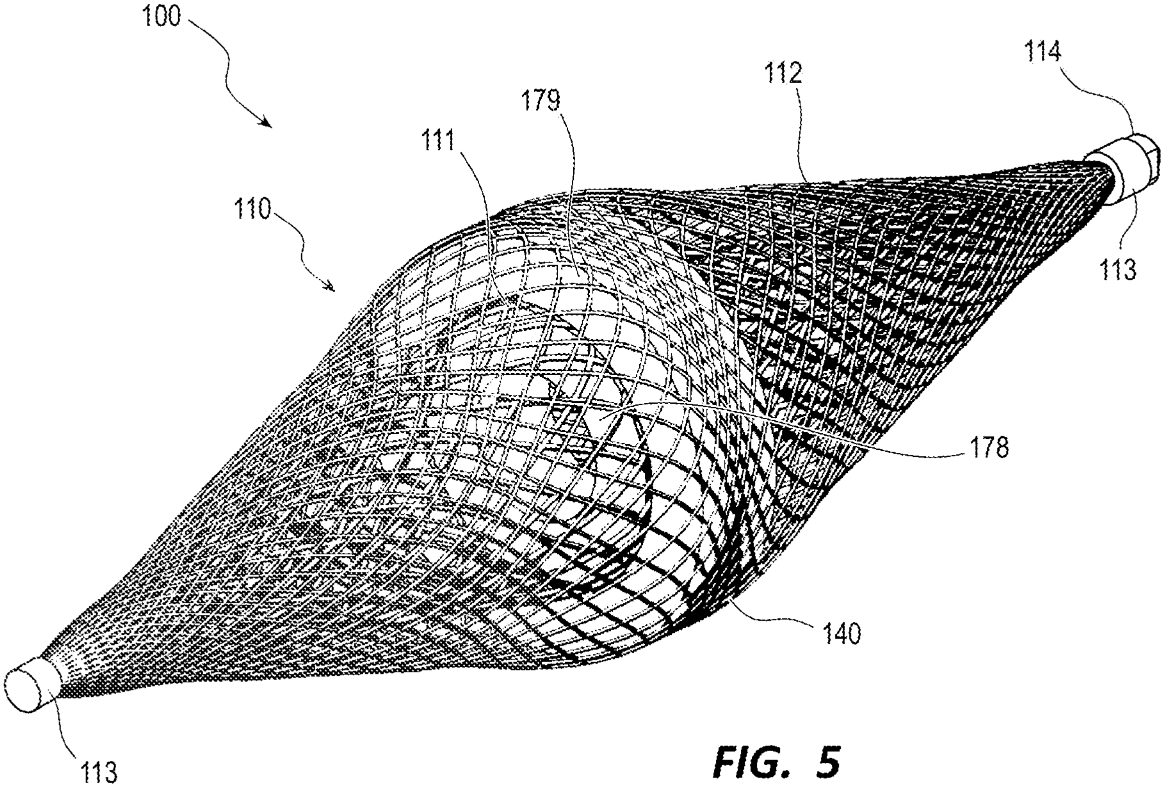
FIG. 5 is a perspective view of the braided medical device of FIG. 1A during the manufacturing process of FIG. 4, with ring-shaped inserts disposed inside an inner braided layer and an outer braided layer.
Figure 5A:
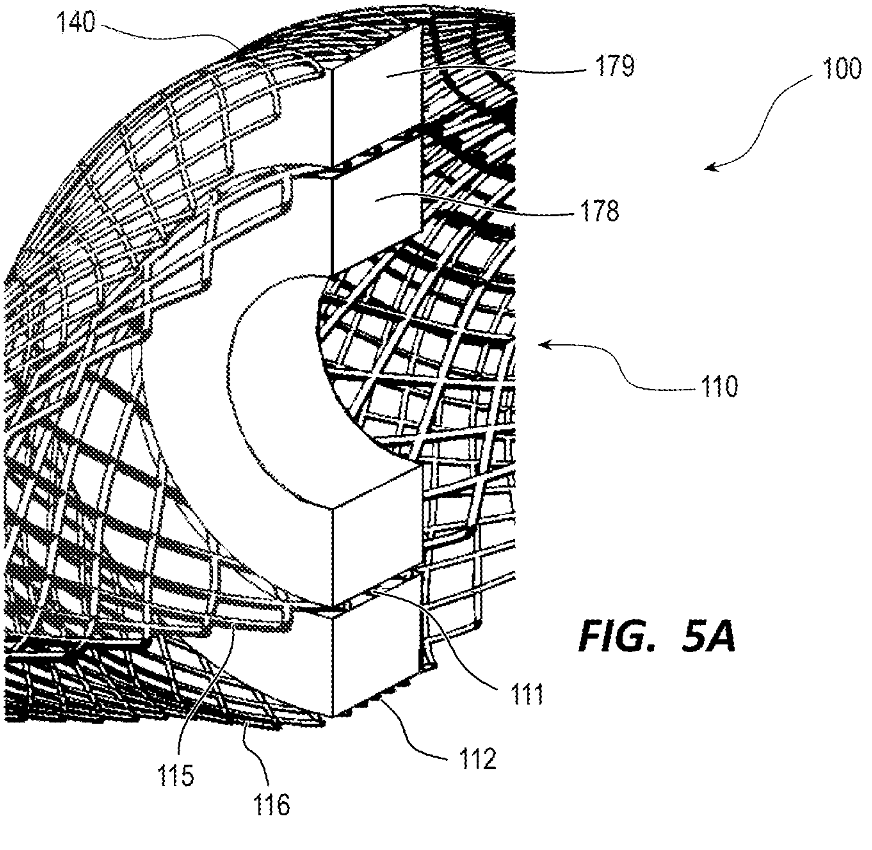
FIG. 5A is a close-up cross-sectional view of the braided medical device of FIG. 5A, with the ring-shaped inserts disposed inside the inner braided layer and the outer braided layer.
Figure 6:
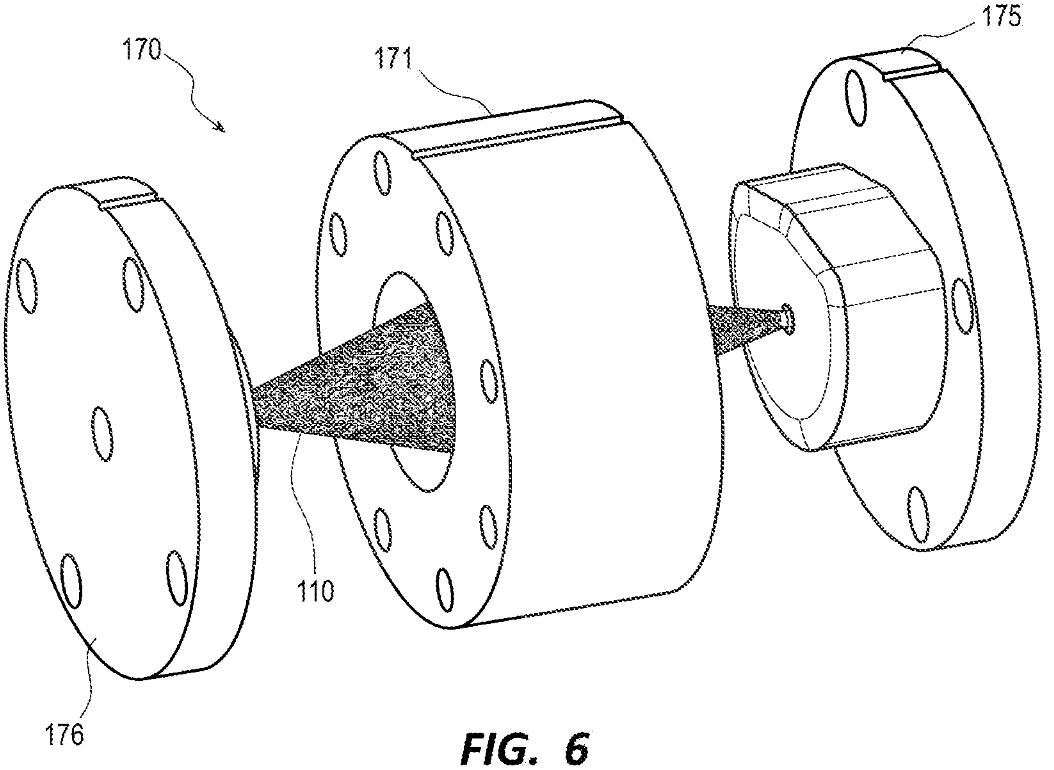
FIG. 6 is a perspective view of an embodiment of a forming mold of the manufacture process of FIG. 4 with the braided medical device of FIG. 5A disposed within the forming mold and the forming mold in an open state.
Figure 6A:
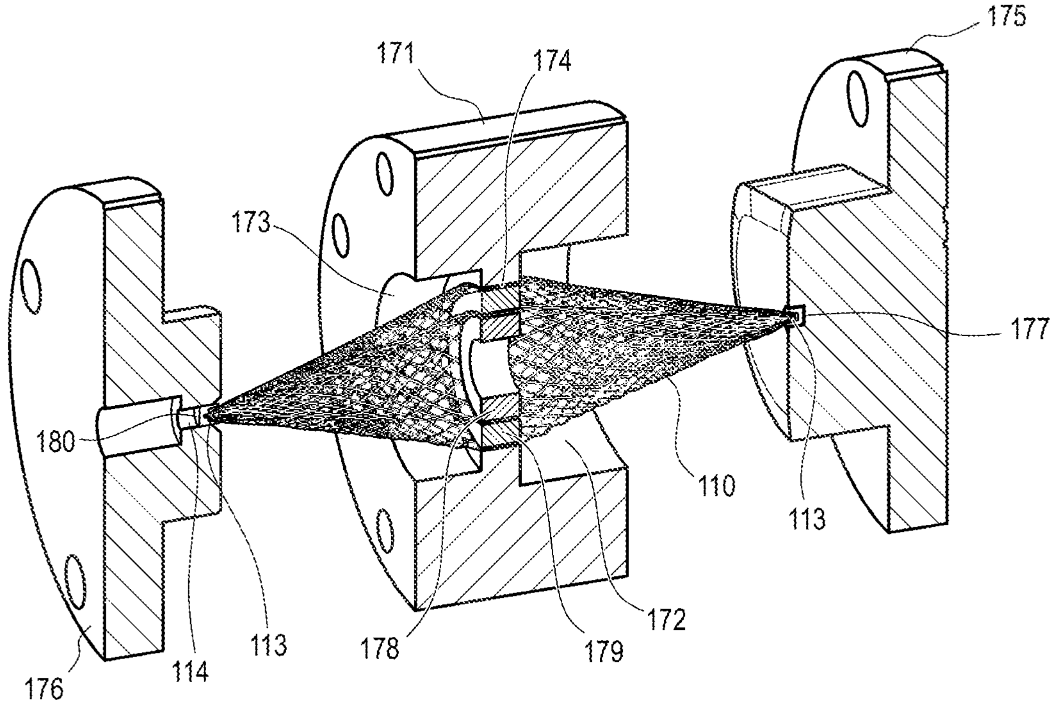
FIG. 6A is a cross-sectional view of the forming mold of FIG. 6A with the braided medical device of FIG. 5A disposed within the forming mold and the forming mold in the open state.

FIGS. 1A, 1B, and 2 illustrate an embodiment of a braided medical device configured for treating a VSD. FIG. 3 illustrates a human heart with a VSD and FIG. 3A illustrates a braided medical device disposed within the VSD. FIG. 4 illustrates a flow chart of an embodiment of a manufacturing process for making the braided medical device. FIGS. 5 and 5A illustrate a braided medical device during the manufacturing process with ring-shaped inserts disposed inside an inner braided layer and an outer braided layer. FIGS. 6 and 6A illustrate an embodiment of a forming mold of the manufacture process of FIG. 4 with the braided medical device of FIG. 5 disposed within the forming mold and the forming mold in an open state. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

Referring to FIGS. 1A and 1B, a diagrammatic representation of one embodiment of a braided medical device 100 is illustrated in perspective and side cross-sectional views, respectively. In this embodiment, the braided medical device 100 is designed for insertion into, and closure of, a VSD in the human heart. In other embodiments, the braided medical device 100 may be configured to occlude other openings, repair other defects, or for use in any other suitable medical procedure. During use, the braided medical device 100 may be delivered in a radially collapsed state through a delivery catheter to the heart and then released from the catheter and thus allowed to expand to its original shape (such as the shape shown in FIGS. 1A and 1B) to occlude a VSD. In the illustrated embodiment, the braided medical device 100 includes a frame 110 including a left disc 120, a central waist 140, and a right disc 130. The waist 140 is configured to straddle the ventricular septum of the heart, thus filling the cardiac defect, while the left disc 120 lies in the left ventricle, and the right disc 130 lies in the right ventricle.

In the illustrated embodiment, the frame 110 is constructed from two layers of braided wires, an inner braid layer 111 and an outer braid layer 112. The braided wires may be formed from any suitable shape memory metal alloys, such as nickel-titanium, copper-aluminum-nickel, copper-zinc-aluminum, etc. In certain embodiments, the braided wires are formed from Nitinol. In other embodiments, the braided wires can be formed from any suitable shape memory polymer, shape memory composite, or shape memory hybrid. In the illustrated embodiments, the inner and outer braid layers 111, 112 are in contact with each other at various locations of the left disc 120 and the right disc 130. The waist 140, which connects the left and right discs 120, 130, is cylindrical, and there is a separation or a space 141 between the inner and outer braid layers 111, 112. The inner braid layer 111 may have a greater stiffness than the outer braid layer 112. This configuration may gently fill the VSD and prevent damage or injury to the ventricular septum, as the softer outer braid layer 112 is in contact with the ventricular septum, while maintaining structural support of the braided medical device 100, in part due to support form the inner braid layer 111. For example, the stiffness of the inner braid layer 111 may be from about 2 times to about 10 the stiffness of the outer braid layer 112. To achieve this difference in stiffness, in some embodiments, a diameter of the braided wires of the inner braid layer 111 can be larger than a diameter of the outer braid layer 112. For example, in an embodiment, the diameter of the braided wires of the inner braid layer 111 can range from about 0.0025 inches to about 0.004 inches and the diameter of the braided wires of the outer braid layer 112 can range from about 0.0015 inches to about 0.0025 inches. The right disc 130 may be circular and flat.

The braided medical device 100 may also include a radiopaque marker band 113 crimped, swaged and/or welded onto each end of the frame 110 for radiographic visibility during and after implant. The radiopaque marker band 113 may be formed from any suitable material, such as platinum-iridium alloy, tantalum, tungsten, or gold. Other materials are contemplated within the scope of this disclosure. A threaded connector 114 may also be welded or otherwise coupled onto one of the radiopaque marker bands 113 for connection to a delivery wire that is used to advance the braided medical device 100 through a delivery catheter to a treatment location, such as the heart. The threaded connector 114 can be formed from any suitable material, such as stainless steel or titanium. Other materials are contemplated within the scope of this disclosure. In some embodiments, a fabric 117 may be sewn into, or otherwise coupled to, the left and/or right discs 120, 130 and/or into the waist 140, to expedite occlusion of the VSD. The fabric can include any suitable material, including polyester. Other materials are contemplated within the scope of this disclosure.

The braided medical device 100 may be configured with a shape designed to help the braided medical device 100 stay in place within (and occlude) a VSD. For example, in the illustrated embodiment of FIG. 2, an upper portion of the left disc 120 is non-circular and flat. The left disc 120 includes a top edge 122, top corners 123, upper edges 127 disposed between the top edge 122 and the top corners 123, side portions 124, and a bottom portion 125. As shown in FIG. 2, an empty region 126 represents surface area of the left disc 120 that would exist if the left disc 120 was fully circular. A Distance A extends from a perimeter 142 of the waist 140 to the top edge 122 of the left disc 120. The Distance A is configured such that the braided medical device 100 can be implanted in a VSD with a subaortic rim having a narrow width. For example, in some embodiments, the Distance A may range from about one millimeter to about four millimeters. A Distance B extends from the perimeter 142 of the waist 140 to the top corners 123 of the left disc 120. The Distance B is greater than the Distance A, so some of the surface area, stability, retention, and holding power lost to the empty region 126 is regained and dispersed away from the top edge 122 that will sit directly underneath the aortic valve on the subaortic rim. Retention may be a result of engagement of the ventricular septum on both sides and inferior to the VSD by the left and right discs 120, 130. The shape of the left disc 120 allows additional surface area engagement of the ventricular septum on the left ventricle side and superior to the VSD by the left disc 120 to prevent the top edge 122 from tipping into or though the VSD as a result of left ventricular pressure acting on the left disc 120. Stability may be important both during and after the implant procedure. The left disc 120 with increased surface area and holding power on the side portions 124 and bottom portion 125 may also help mitigate any instability caused by the soft outer braid layer 112 of the waist 140. The upper edges 127 may be angled to allow for some error or tolerance in the orientation of the braided medical device 100 during and after implant. An angle α can range from about zero degrees to about 15 degrees and may be about ten degrees. Despite the empty region 126, the overall shape of the left disc 120 may be round enough to allow for self-orientation with a delivery system.

A Distance C extends from a central point 128 to the perimeter 142 of the waist 140 and is equivalent to a radius of the waist 140. The Distance C can range from about one millimeter to about 14 millimeters. A Distance D extends from the central point 128 to an outer edge 132 of the right disc 130 and is equivalent to a radius of the right disc 130. The Distance D can range from about four millimeters to about 20 millimeters. In the illustrated embodiment, the central point 128 is radially offset toward the bottom portion 125 of the left disc 120 when the left disc 120 is considered as having a fully circular shape and is in alignment with a central axis of the right disc 130 and a central axis of the waist 140.

Referring now to FIG. 3, a cross-sectional view of a human heart 150 with a VSD 154 is illustrated. The VSD 154 allows blood from a left ventricle 151 of the heart 150 (oxygenated blood) to flow into a right ventricle 152 through the VSD 154 (as shown by curved arrow). This can cause a number of health problems, including but not limited to failure to survive, enlargement of the heart, inefficiency of the heart, patient tires easily, etc.

FIG. 3A shows a close-up of the VSD 154 of FIG. 3, with a braided medical device 100 implanted in the heart 150 to repair and occlude the VSD 154. As depicted, the VSD 154 is adjacent an aortic valve 155, which can cause challenges for braided medical devices with a circular left disc. For example, it can present a challenge due to the relatively small width of a subaortic rim 156 of the heart due to the position of the aortic valve 155 with respect to the VSD 154. The proximity of the aortic valve 155 can limit the size of the subaortic rim 156 available for an upper portion of a circular left disc of an occlusion device to fix against. If the left disc 120 is circular and concentric to the waist 140 it has to be large enough to provide sufficient holding power against the septal wall to resist falling into the right ventricle 152 but at the same time small enough to avoid impingement of the aortic valve 155.

As illustrated in FIG. 3A, the braided medical device 100 is disposed within the VSD 154. The left disc 120 of the frame 110 is located within the left ventricle 151, the right disc 130 is located within the right ventricle 152, and the waist 140 is located within the VSD 154. The top edge 122 of the left disc 120 is positioned on a left ventricle side of the subaortic rim 156 of the aortic valve 155. The non-circular shape of the left disc 120, as previously described, may thus permit the top edge 122 to be positioned on the subaortic rim 156 without causing harm or damage to the aortic valve 155. The bottom portion 125 of the left disc 120 is positioned on a left ventricle side of a ventricular septum 153. Also, as shown in FIG. 3A, the bottom portion 125 and lateral portions of the left disc 120 may provide surface area for contacting the anatomy and stabilizing the braided medical device 100 within the VSD 154, while the top edge 122 is configured to avoid interference with the aortic valve 155. Additionally, a top portion of the right disc 130 is positioned on the right ventricle side of the subaortic rim 156 and a bottom portion of the right disc 130 is positioned on the right ventricle side of the ventricular septum 153. The soft outer braid layer 112 of the waist 140 is in contact with a perimeter of the VSD 154 to minimize forces that may result in harm or damage to the ventricular septum 153.

Referring now to FIG. 4, one embodiment of a method 200 for making a braided medical device is outlined in a flow chart. The braided medical device may be a VSD closure device, such as the one described above, or any other suitable braided device. In step 1 202, an inner insert is placed inside a first discrete length of a braid 115 that is configured to be the stiff inner braid layer 111 of the braided medical device 100, as depicted in FIGS. 5 and 5A. In an embodiment, an inner insert 178 is formed from calcium sulfate dihydrate (e.g., gypsum). In other embodiments, the inner insert 178 may be formed from any other suitable material that can be broken of dissolved into pieces or particles. The inner insert 178 forms a void in the center of the braided medical device 100.

In step 2 204, an outer insert 179 is placed over the first discrete length of the braid 115 and the inner insert 178 as depicted in FIGS. 5 and 5. In an embodiment the outer insert 179 is formed from calcium sulfate dihydrate (e.g., gypsum). In other embodiments, the outer insert 179 may be formed from any other suitable material that can be broken of dissolved into pieces or particles. The outer insert 179 forms a separation between the first discrete length of the braid 115 and a second discrete length of a braid 116 at the waist 140 of the frame 110.

In step 3 206, the discrete length of the braid 116 is placed over the outer insert 179 as shown in FIGS. 5 and 5A. The second discrete length of the braid 116 is configured to be the soft outer braid layer 112 of the braided medical device 100 that will contact a perimeter of the VSD. The softness of the defect contacting outer braid layer 112, relative to the stiffness of the non-defect contacting inner braid layer 111, is configured to minimize forces on the VSD to minimize the potential to cause heart block.

In step 4 208, the radiopaque marker bands 113 are placed over the first and second discrete lengths of braids 115, 116 at both ends of the frame 110, as illustrated in FIG. 5, and positioned a specific distance apart. For example, the distance between the radiopaque marker bands 113 can range from about 25 millimeters to about 50 millimeters. A volume of the frame 110 between the two radiopaque marker bands 113 is an amount necessary to properly fill a forming mold, so that after the frame 110 is removed from the forming mold, outer dimensions of the frame 110 match inner dimensions of the forming mold.

In step 5 210, the radiopaque marker bands 113 are crimped to secure them to the frame 110. They are swaged to reduce their diameter and gather the braided wires into a tight bundle in preparation for welding. The excess wire protruding from the radiopaque marker bands 113 is trimmed back to a specific length. Remaining excess wire at either end of the frame 110 is welded to form a dome with the radiopaque marker bands 113.

In step 6 212, the threaded connector 114 is welded onto one of the radiopaque marker bands 113, as depicted in FIG. 5. The threaded connector 114 facilitates connection of a delivery wire, which will be used to advance the braided medical device 100 to the heart 150 through a catheter. It also allows the braided medical device 100 to be recaptured into the catheter and redeployed or removed entirely from the body.

In step 7 214, the frame 110 is loaded into a forming mold 170, as illustrated in FIGS. 6 and 6A, which will constrain the frame 110 and define its outer shape while the inner and outer inserts 178, 179 will constrain and define an inner shape. As illustrated, the forming mold 170 includes a center section 171, a left disc end cap 175, and a right disc end cap 176. The center section 171 includes a left disc cavity 172 for forming the non-round left disc 120. A shape of the left disc cavity 172 is configured to match the external shape of the non-round left disc, as previously described. The center portion 171 further includes a right disc cavity 173 and a waist cavity 174 having shapes to match external shapes of the right disc 130 and waist, as previously described. The left disc end cap 175 includes a radiopaque marker band cavity 177 configured to receive the radiopaque marker band 113 coupled to the frame 110 adjacent the left disc 120. The right disc end cap 176 includes a radiopaque marker band cavity 180 configured to receive the radiopaque marker band 113 and threaded connector 114 coupled to the frame 110 adjacent the right disc 130.

In step 8 216, the forming mold 170 is heated to a temperature high enough to affect a phase transformation in the material of the braided wires (e.g., Nitinol). In some embodiments, the forming mold 170 may be heated to a temperature ranging from about 450 degrees Centigrade to about 550 degrees Centigrade. During heating, the inner and outer inserts 178, 179 may undergo a thermal degradation process known as calcination, which will ease their later dissolution and removal from the frame 110. The forming mold 170 is quenched to rapidly reduce the temperature and set the final shape of the braided medical device 100. The forming mold 170 is opened, and the braided medical device 100 is removed from the forming mold 170.

In step 9 218, using running water, the inner and outer inserts 178, 179 are softened and dissolved out of the braided medical device 100 with minimal manipulation and impact to the integrity of the braided medical device 100. The dissolution process can be expedited by crushing/breaking the inner and outer inserts 178, 179 prior to wetting.

In step 10 220, the braided medical device 100 is cleaned, typically in alcohol, and then depyrogenated with heat, to remove any pyrogens that could later cause patient harm.

In step 11 222, the fabric (e.g., polyester) is sewn into the left and right discs 120, 130 and into the waist 140 of the braided medical device 100. The fabric is configured to function as a scaffold for endothelialization over the surface of the braided medical device 100, leading ultimately to closure of the VSD.

In step 12 224, the completed braided medical device 100 is packaged, sterilized, and shipped to a user.

In various alternative embodiments, many of the above-described steps of the method 200 may be altered, omitted, and/or changed in order, and/or other steps may be added, without departing from the scope of the present disclosure. For example, in one embodiment, the braided medical device might only include one layer of braided material and thus only one insert may be used. In another embodiment, more than two inserts may be used. Some embodiments might not include radiopaque marker bands. In some embodiments, the ends of the braided medical device might be closed via any suitable alternative technique(s). Some embodiments might not include the fabric, so that step is also optional. In its simplest form, the method may involve simply forming a braided material over an insert, completing formation and processing of the braided medical device over the insert, dissolving the insert, and then completing any remaining necessary device processing. The method outlined in FIG. 4, therefore, is but one example of a method for making one braided medical device embodiment.

FIGS. 5 and 5A illustrate the braided medical device 100 at the point in the method 200 where the inner insert 178 is placed inside the first discrete length of the braid 115 and the outer insert 179 is placed inside the second discrete length of the braid 116 and over the inner insert 178 such that the first length of the braid 115 is disposed between the inner insert 178 and the outer insert 179. The inner and outer inserts 178, 179 may be produced by any suitable method or combination of methods, including but not limited to casting, extruding, machining, 3D printing, or the like. Further, the radiopaque marker bands 113 and the threaded connector 114 are coupled to the frame 110.

FIGS. 6 and 6A illustrate the frame 110 within the forming mold 170 to constrain the frame 110 while it is being heated to set the final shape. The frame 110 is positioned inside the center section 171. The inner and outer inserts 178, 179 are positioned in the center section 171. The radiopaque marker bands 113 and the threaded connector 114 are positioned in marker band cavities 177, 180 of the left and right disc end caps 175, 176. The left and right disc end caps 175, 176 are moved toward the center section 171 so the frame 110 compresses and flattens to take the shape of the left and right disc cavities 172, 173.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, a method for making a braided medical device may include one or more of the following steps positioning a frangible insert inside a braided structure; processing the braided structure to form the braided medical device; and removing the frangible insert from the braided medical device. Other steps are also contemplated.

In the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

It will be appreciated that various features are sometimes grouped together in a single embodiment, figure, or description thereof for the purpose of streamlining the disclosure. Many of these features may be used alone and/or in combination with one another.

The phrase "coupled to" refers to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

References to approximations are made throughout this specification, such as by use of the term "about." For each such reference, it is to be understood that, in some embodiments, the value, feature, or characteristic may be specified without approximation. For example, where the qualifiers "about" is used, these terms include within their scope the qualified word in the absence of their qualifier.

The terms "a" and "an" can be described as one, but not limited to one. For example, although the disclosure may recite a housing having "a stopper," the disclosure also contemplates that the housing can have two or more stoppers.

Unless otherwise stated, all ranges include both endpoints and all numbers between the endpoints.

Recitation in the claims of the term "first" with respect to a feature or element does not necessarily imply the existence of a second or additional such feature or element.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A method for making an implantable braided medical device, the method comprising:
- positioning a ring-shaped frangible insert inside a braided structure;
- processing the braided structure to form the implantable braided medical device; and
- removing the frangible insert from the braided medical device.

2. The method of claim 1, wherein the frangible insert comprises an annular configuration that is configured to form a void in a center of the braided medical device.

3. The method of claim 1, further comprising attaching a radiopaque marker band to the braided structure at least one end of the braided medical device.

4. The method of claim 3, wherein attaching the radiopaque marker band comprises one or more of crimping, swaging, and welding.

5. The method of claim 1, wherein the frangible insert is configured to constrain and define an inner shape of the braided structure during processing.

6. The method of claim 1, wherein processing the braided structure comprises:
- loading the braided structure into a forming mold;
- heating the forming mold to a temperature high enough to affect a phase transformation in a material of the braided structure and calcination of the frangible insert; and
- quenching the forming mold.

7. The method of claim 1, wherein removing the frangible insert comprises crushing the frangible insert into multiple pieces and washing the multiple pieces out of the braided medical device with water.

8. The method of claim 1, wherein removing the frangible insert comprises dissolving the frangible insert with water.

9. The method of claim 1, further comprising sewing a fabric onto the braided medical device.

10. The method of claim 1, wherein the braided medical device comprises a closure device for a heart defect.

11. A method for making a braided medical device, the method comprising:
- positioning a ring-shaped frangible insert inside a braided structure;
- processing the braided structure to form the braided medical device;
- removing the frangible insert from the braided medical device; and
- attaching a radiopaque marker band to the braided structure at least one end of the braided medical device.

12. A method for making a braided medical device, the method comprising:
- positioning a ring-shaped frangible insert inside a braided structure;
- loading the braided structure into a forming mold;
- heating the forming mold to a temperature high enough to affect a phase transformation in a material of the braided structure and calcination of the frangible insert; and
- quenching the forming mold; and
- removing the frangible insert from the braided medical device.

* * * * *